(12) United States Patent
Gaida et al.

(10) Patent No.: US 7,416,163 B2
(45) Date of Patent: Aug. 26, 2008

(54) SUPPORT

(75) Inventors: Gerhard Gaida, Aalen (DE); Roland Brenner, Wallhausen (DE)

(73) Assignee: Carl Zeiss Surgical GmbH, Oberkochen (DE)

(*) Notice: Subject to any disclaimer, the term of this patent is extended or adjusted under 35 U.S.C. 154(b) by 67 days.

(21) Appl. No.: 09/967,769

(22) Filed: Sep. 28, 2001

(65) Prior Publication Data

US 2002/0074472 A1  Jun. 20, 2002

(30) Foreign Application Priority Data

Sep. 30, 2000  (DE)  ................................  100 48 545

(51) Int. Cl.
*F16L 3/00* (2006.01)

(52) U.S. Cl. ................ 248/325; 248/123.11; 248/276.1

(58) Field of Classification Search ................ 248/648, 248/123.2, 182.1, 184.1, 183.2, 276.1, 297.11, 248/325, 364, 334.1, 280.11; 600/425, 429; 378/20

See application file for complete search history.

(56) References Cited

U.S. PATENT DOCUMENTS

| | | | |
|---|---|---|---|
| 3,210,114 A | 10/1965 | Lawton | ........................ 294/81 |
| 3,396,931 A | 8/1968 | Eckstein | ..................... 248/280 |
| 3,891,301 A * | 6/1975 | Heller | ........................ 359/384 |
| 3,945,597 A | 3/1976 | Klein | |
| 4,266,747 A | 5/1981 | Souder, Jr. et al. | |
| 4,296,906 A | 10/1981 | Matthijsse | |
| 4,339,100 A * | 7/1982 | Heller et al. | ............. 248/123.2 |
| 4,344,595 A * | 8/1982 | Heller et al. | ................. 248/542 |
| 4,364,535 A | 12/1982 | Itoh et al. | |
| 4,548,373 A | 10/1985 | Komura | |
| 4,741,607 A * | 5/1988 | Heller | ........................ 359/384 |
| 5,144,025 A | 9/1992 | Tentorio | |
| 5,173,802 A * | 12/1992 | Heller | ........................ 359/384 |
| 5,205,522 A * | 4/1993 | Nakamura | ............. 248/123.11 |
| 5,273,039 A * | 12/1993 | Fujiwara et al. | ............. 600/407 |
| 5,332,181 A * | 7/1994 | Schweizer et al. | ..... 248/123.11 |

(Continued)

FOREIGN PATENT DOCUMENTS

DE  39 37 631 A1  5/1991

(Continued)

OTHER PUBLICATIONS

European Patent Office, European Search Report, EP 01 12 0922, Aug. 14, 2003.

*Primary Examiner*—Korie Chan
*Assistant Examiner*—Steven M. Marsh

(57) ABSTRACT

A support is designed to receive an operation microscope. This support has a support column, movable around a rotation axis, with a first carrier arm and a second carrier arm which, with respect to the first carrier arm, can be moved around a first pivot axis and a second pivot axis. A cable connection is provided for producing a restoring force for the second carrier arm, and couples the second carrier arm to a counterweight for producing a restoring force around the second pivot axis. The counterweight is arranged in the region of the support column, to minimize inertial action accompanying a movement of the support around the rotation axis. A freewheel rotary joint is provided in the cable connection to suppress a feedback to the counterweight of a movement of the second carrier arm around the first pivot axis.

7 Claims, 2 Drawing Sheets

U.S. PATENT DOCUMENTS

| | | | |
|---|---|---|---|
| 5,435,515 A * | 7/1995 | DiGiulio et al. | 248/576 |
| 5,480,114 A * | 1/1996 | Nakamura | 248/123.2 |
| 5,494,034 A | 2/1996 | Schlondorff et al. | |
| 5,609,316 A * | 3/1997 | Tigliev | 248/123.11 |
| 5,651,718 A * | 7/1997 | Nakamura | 248/123.2 |
| 5,667,186 A * | 9/1997 | Luber et al. | 248/550 |
| 5,818,638 A * | 10/1998 | Nakamura | 359/384 |
| 2002/0121577 A1 | 9/2002 | Metelski | 248/123.11 |

FOREIGN PATENT DOCUMENTS

| | | |
|---|---|---|
| DE | 198 20 710 A1 | 11/1999 |
| DE | 198 20 710 A1 | 11/1999 |
| DE | 200 19 105 U1 | 12/2000 |
| DE | 2001 14 343 U1 | 1/2002 |
| DE | 101 42564 A1 | 4/2002 |
| EP | 0 293 228 A2 | 5/1988 |
| EP | 0 628 290 A1 | 12/1993 |
| EP | 0 628 290 B1 | 12/1994 |
| GB | 2 074 337 A | 4/1980 |
| JP | 04-13591 | 1/2004 |
| WO | WO 81/03054 | 4/1981 |
| WO | WO 97/13997 | 4/1997 |

* cited by examiner

SUPPORT

Cross-References to Related Applications

Not applicable.

STATEMENT REGARDING FEDERALLY SPONSORED RESEARCH OR DEVELOPMENT

Not applicable.

BACKGROUND OF THE INVENTION

The invention relates to a support, in particular a support to receive a medical device, for example an operation microscope, with a first carrier arm and a second carrier arm, the second carrier arm being mounted on a first shaft and a second shaft for pivoting with respect to the first carrier arm, and coupling means are provided which couple the second carrier arm to a means for the production of a restoring force around at least one of the shafts.

Technical Field

Such a support is known from U.S. Pat. No. 5,494,034. A floor support is described there which includes a support column on which a carrier apparatus with a first and a second carrier arm is arranged. The first carrier arm is rotatably mounted on the support column. The second carrier arm is pivotably fastened to an end region of the first carrier arm and is movable with respect to two axes orthogonal to the first carrier arm. U.S. Pat. No. 5,494,034 furthermore discloses a ceiling support with a support column which is secured to a ceiling. A compensating weight is provided on this support column, and is received on a lever arm and with this can be rotated around the support column. This lever arm is coupled to a carrier arm device of first and second carrier arms by means of a toothed belt transmission. The first carrier arm of the carrier arm device is pivotably mounted on the support column. The second carrier arm is furthermore pivotably arranged on the first carrier arm. A medical device is mounted on the second carrier arm. The weight of the medical device received on the second carrier arm is fully compensated by means of the compensating weight.

A support for an operation microscope is described in EP 0 293 228 B1 in which a rod mechanism is provided for coupling the operation microscope and counterweights. By means of these counterweights it is possible to balance the support, and thus to move the operation microscope substantially free of weight forces.

A floor support with weight compensation to receive an operation microscope is known from WO 97/13997. This support has a support column on which a carrier arm device with first and second carrier arms is received. The first carrier arm is pivotably fastened to the support column. The second carrier arm is furthermore rotatably mounted on the first carrier arm. The operation microscope is received in an end region of the second carrier arm. Respective counterweights are provided on the first and second carrier arm to compensate the weight acting on the operation microscope. These counterweights balance the first and second carrier arms on the principle of a beam balance.

SUMMARY OF THE INVENTION

The invention has as its object to provide a support which on the one hand has space-saving dimensions, and on the other hand, however, makes it possible for a heavy medical device received on the support to be easily moved in optional directions.

This object is attained by a support with the following features: a support column, a first carrier arm, a second carrier arm mounted pivotably with respect to the first carrier arm, on a first axis and a second axis, a restoring device for producing a restoring force around at least one of the first axis and the second axis, a coupling device that couples the second carrier arm with the restoring device, and a suppressing device for suppressing feedback of movement of the second carrier arm around at least one of the first axis and the second axis. The restoring device comprises a weight that moves in a region of the support column.

As a development of the invention, the device which prevents a feedback of a movement of the second arm around at least one of the two axes to the restoring device for producting a restoring force is associated with the coupling device. A support is provided in this manner in which a restoring moment for one axis for the compensation of a corresponding loading of the support brings about no effects of any kind on the movability of the support around another axis.

As a development of the invention, the means for the production of a restoring force comprises a weight. This weight acts as a counterweight. In this manner, while retaining a simple construction, a restoring force for a different weight of the medical device received on the support can be set by increasing or decreasing the counterweight.

As a development of the invention, the means for the production of a restoring force comprises a weight which is movable in the region of a support column. By a weight which is movably arranged in the region of a support column, there is to be understood a weight which is situated near to or in the support column and whose position there can be altered. In that it is arranged on or immediately near a rotation axis of the support column, inertial forces can be minimized which arise on rotating the support around the rotation axis of the support column. These inertial forces have their origin in the weight and oppose the related support movement around the corresponding rotation axis with a counter-moment. Such an arrangement of the weight thus ensures an easy rotatability of the support around an axis of the support column. Moreover, a support which is stable to tilting and has a low center of gravity of the equipment can also be thus provided.

As a development of the invention, the means for coupling is constituted as a connecting cable. The means for coupling can easily be matched to a desired support geometry in this manner.

As a development of the invention, the means for coupling is constituted as a rod arrangement. A support is provided in this manner which withstands high mechanical loadings.

As a development of the invention, the means for the production of a restoring force compensates a weight acting on the second arm due to a load arranged on it. It is possible in this manner to completely balance the support so that a medical device received on the support can be moved almost without force.

As a development of the invention, a compensating restoring force is transmitted in the support by means of the connecting cable in the support, and acts on the second arm at a distance from the support column, the connecting cable being deflected into a direction parallel to the support column. In this manner, a counterweight can be arranged in the region of the support column in order to thus provide a support which is stable to tilting and whose center of gravity is situated in the region of the support column.

As a development of the invention, a deflection means for guiding the connecting cable is provided in the neighborhood of a support column. It is possible in this manner to guide a compensating weight in the support column.

As a development of the invention, the first carrier arm is rotatable in the support around a rotation axis which is substantially parallel to the support column. A support with a large working range is provided in this manner.

As a development of the invention, the coupling means is interrupted at least once, and the means for suppressing a feedback of a movement is constituted as a rotation decoupling. Easy movability of the support is ensured in this manner. In particular with the use of a connecting cable as the coupling means, or of a rod arrangement, twisting or torsion of the connecting cable or rod is prevented.

As a development of the invention, the means for the suppression of a feedback of a movement of the second arm is constituted as a freewheel rotary joint. It is possible in this manner to prevent the twisting of a connecting cable as the coupling means.

As a development of the invention, the first axis is substantially orthogonal to the second axis. By a substantially orthogonal orientation of the first and second axes is to be understood an orientation of these axes in which, within a tolerance interval of ±20°, they are mutually perpendicular. A carrier arm system with two degrees of freedom of movement is provided in this manner, whose functioning can easily be comprehended by a user of the support.

As a development of the invention, the first and second arms are arranged at a distance from one another. A mechanically simple constructional form of the support joints is made possible in this manner.

As a development of the invention, the freewheel rotary joint is situated on one of the axes. In this manner, a swivel block can be used as the freewheel rotary joint, and effects the nearly complete suppression of a feedback.

As a development of the invention, the connecting cable is at least sectionally guided along one of the axes by means of rollers. A particularly low-friction cable guidance is provided in this manner.

As a development of the invention, the means for feedback is constituted as a rod which comprises a transmission rod displaceable along one of the axes. It is possible in this manner to use a lever action brought about by a counterweight as the restoring force for a medical device arranged on the support.

As a development of the invention, the support includes, as means for the production of a restoring force, a lever arm which is arranged on one of the carrier arms and which carries a counterweight, the coupling means coupling a pivoting movement of the lever arm to a pivoting movement of the second carrier arm. It is possible in this manner to compensate a load moment that varies with a varying position of the medical device with a counter-moment matched to the load moment.

As a development of the invention, the support is constituted as a floor support. An easily transportable support is provided in this manner.

If the support with this constructional form is constituted as a ceiling support, a particularly space-saving support construction is provided.

BRIEF DESCRIPTION OF THE DRAWINGS

Further features and advantages of the invention are shown in the accompanying drawings and are described hereinafter.

DETAILED DESCRIPTION OF THE INVENTION

Figure 1:
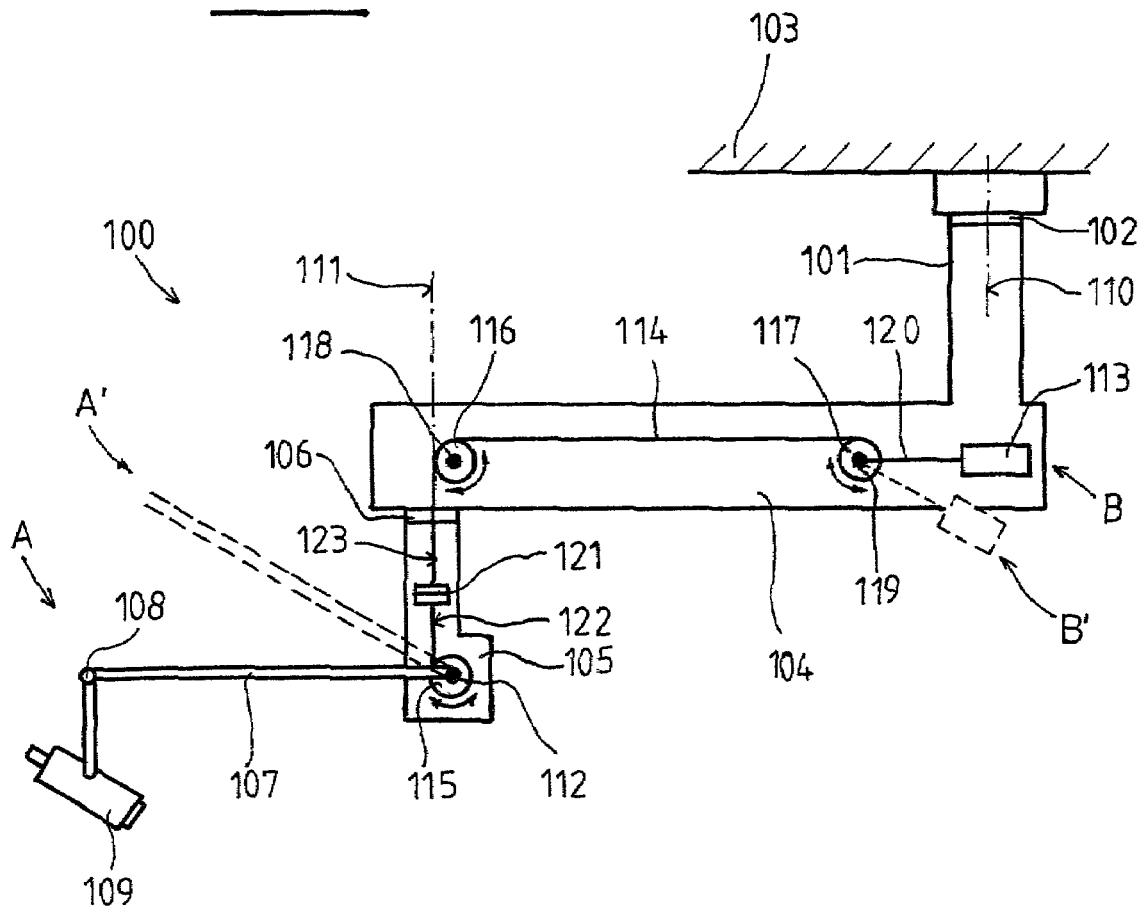
FIG. 1 shows a first embodiment of a support.

FIG. 1 shows a support 100 constituted as a ceiling support and suspended on a ceiling 103 by means of a support column 101 with a rotary joint 102, for example, in an operating theater. As an alternative to embodying the support 100 as a ceiling support, it is also possible, while retaining the essential principle of construction, to constitute this as a floor support. In this case, for example, the support column 101 with rotary joint 102 is mounted on a suitable support foot.

The support column 101 is connected to a first carrier arm 104 which acts as the supporting arm, and on which a second carrier arm 107 is received in an end region by means of a lift arm carrier 105 with a rotary joint 106. This second carrier arm 107 acts as the lifting arm. It has a joint 108 in an end region, on which an operation microscope 109 is mounted as the medical device.

The carrier arm 104 can be pivoted around a rotation axis 110 parallel to the support column because of the rotary joint 102 on the support column 101. The rotary joint 106 in the lift arm 105 ensures that the second carrier arm 107 is pivotable around a rotation axis 111. The rotation axis 111 then runs substantially parallel to the support column 101, and is situated in the plane of the drawing in the embodiment example explained with reference to FIG. 1. A substantially parallel course of the rotation axis 111 and the support column 101 is also to be understood as a course which deviates from a strictly parallel course, depending for example on manufacturing tolerances, The second carrier arm 107 is pivotably mounted on a pivot shaft 112 on the lift arm carrier 105 at a distance from the first carrier arm 104. This pivot shaft runs, on one hand, orthogonally to the rotation axis 111 of the lift arm carrier 105, and is oriented perpendicular to the plane of the drawing in the Figure. This suspension of the lift arm carrier 105 makes it possible, for example, to move the carrier arm 107 out of a pivoting position A into a pivoting position A' indicated by dashed lines.

A counterweight 113 is provided on the support 100 in order to compensate a weight acting on the operation microscope 109 and bringing about a moment 109 at the pivot axis 112 tending to lower the operation microscope 109. This counterweight 113 serves as the means to produce a restoring force. The counterweight 113 is arranged in the region of the support column 101. An inertial action of the counterweight 113 when there is a movement of the support column 101 with the carrier arms 104 and 107 around the rotation axis 110, in which the counterweight brings about an undesired counter-moment and thus would hinder the movement around the rotation axis 110, is thereby minimized. Furthermore, the overall center of gravity of the support with the operation microscope received is situated in the region of the support column 101 in the neighborhood of the rotation axis 110, and at the rotary joint 102 such bearing forces are minimized which are oriented perpendicular to its rotation axis 110.

The counterweight 113 is connected by means of a connecting cable 114 as coupling means to a deflecting roller 115, by means of which a moment is applied to the pivot axis 112 and compensates the weight of the operation microscope 109. This connecting cable 114 thus couples the counterweight 113 with a movement of the second carrier arm 107 around the pivot axis 112. The connecting cable 114 is guided by the deflecting roller 115 along the rotation axis 111 of the rotary joint 106 in the lift arm carrier 105. It is deflected by means of a deflecting roller 116 toward the first carrier arm 104 and applied to a deflecting roller 117 on which the counter-moment acts which is brought about by the counterweight 113. In the embodiment example shown in FIG. 1, the deflecting rollers 116 and 117 are mounted on rotation axes 118, 119 which are respectively oriented perpendicular to the first carrier arm 104 and to the plane of the drawing. The counterweight 113 acts on the deflecting roller 117 with a lever arm 120. When the second carrier arm 107 moves with an operation microscope 109 received on it from a first pivoting position A into a second pivoting position A' indicated by dashed lines, the counterweight 113 received on the lever arm 120 moves from the position B to the position B', which is correspondingly indicated by dashed lines. In the respective positions of the counterweight 113, the resulting lever arms are matched differently and to the instantaneous position of the second carrier arm 108. This ensures that, in spite of a changing load moment acting on the pivot axis 112, when the second carrier arm 107 is moved from the position A into the position A', exactly the required compensation force is produced by means of the counterweight 113.

A freewheel rotary joint 121 is provided in the connecting cable 114 on the rotation axis 111 in the region of the lift arm 105. This freewheel rotary joint 121 has the effect that the cable of the connecting cable 114 does not twist when the second carrier arm 107 moves around the rotation axis 111. Furthermore, the freewheel rotary joint 121 divides the connecting cable 114 into a section 122 allocated to the second carrier arm 107 and a section 123 which faces toward the counterweight 113. These respective sections 122 and 123 of the connecting cable 114 are thus freely rotatable relative to one another, so that a rotary movement of the second carrier arm 107 around the rotation axis 111 is completely decoupled from a movement of the counterweight 113. In particular, a rotary movement of the second carrier arm 107 around the rotation axis 111 does not lead to a feedback of this rotary movement into the connecting cable section 123 on which the counterweight 113 is arranged. Furthermore, the inertia of the counterweight 113 in a rotation of the second carrier arm 107 around the rotation axis 111 of the rotary joint 106 on the lift arm carrier is minimized by this arrangement of the counterweight 113.

Figure 2:
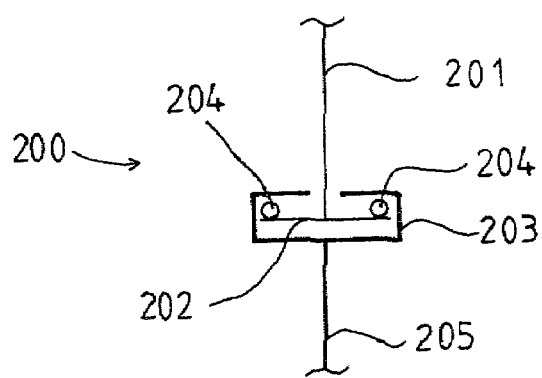
FIG. 2 shows the construction of a free-untwist joint in a support of FIG. 1.

A possible embodiment of the freewheel rotary joint 120 of FIG. 1 is shown in FIG. 2. This freewheel rotary joint is constituted as a ball-bearing rotary joint. The section of the connecting cable 201 facing toward the counterweight 113 of FIG. 1 is connected to a ball carrier plate 202. The section of the connecting cable 205 facing toward the lift arm 107 of FIG. 1 is furthermore fastened to a ball bearing housing 203. Balls 204 are arranged between the ball carrier plate 202 and the ball bearing housing 203. This construction makes it possible for the ball bearing housing 203, together with the section 205 of the connecting cable facing toward the second carrier arm, to turn freely without appreciably twisting the section 201 of the cable connection facing toward the counterweight 113, when the second carrier arm 107 of FIG. 1 rotates around the rotation axis 111.

Instead of constituting the freewheel rotary joint as a ball-bearing rotary joint as explained with reference to FIG. 2, it is also possible to embody this as a swivel block or in another known manner.

Figure 3:
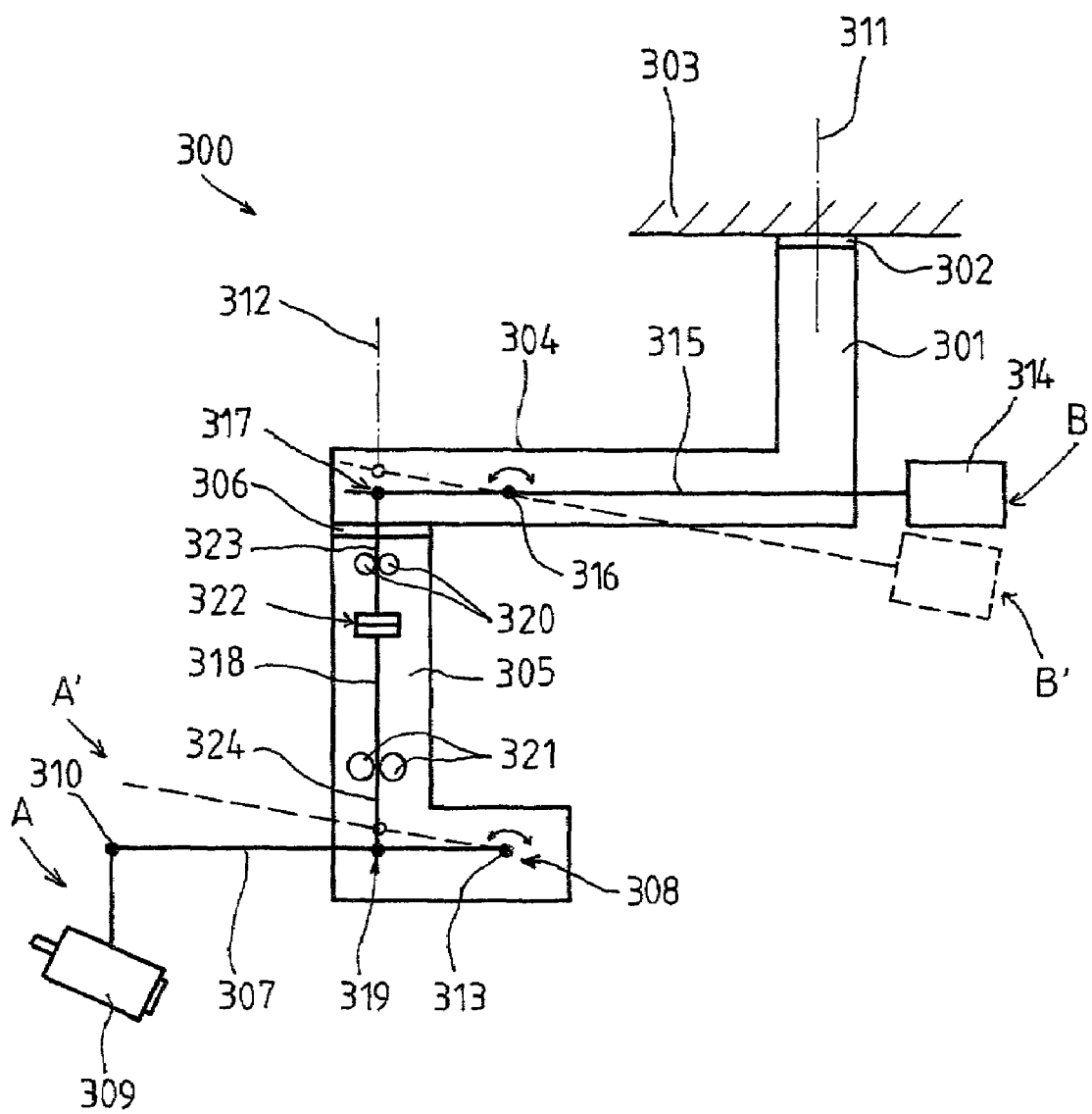
FIG. 3 shows a second embodiment of a support.

FIG. 3 shows, as a further embodiment of the invention, a support 300 whose basic construction corresponds to that of the support 100 of FIG. 1. Like the support of FIG. 1, the support 300 is constituted as a ceiling support and is suspended by means of a support column 301 with rotary joint 302 from a ceiling 303, for example of an operating theater. While retaining the basic construction, it is however also possible to embody the support 300 as a floor support, in which the support column 301 is mounted with the rotary joint 302 on a support foot.

A first carrier arm 304 which acts as a supporting arm is fastened to the support column 301. A lift arm carrier 305 with a rotary joint 306, on which a second carrier arm 307 is received, is associated with this first carrier arm 304. This second carrier arm 307 acts as the lift arm. It is received on the lift arm carrier 305 with a joint 308 and holds, with a joint connection 310, an operation microscope 309 as the medical device.

Corresponding to the support 100 of FIG. 1, the first carrier arm 304 can be pivoted around a rotation axis 311 parallel to the support column by means of a rotary joint 302 on the support column 301. The second carrier arm 307 is movable, with the rotary joint 306 in the lift arm carrier 305, around the rotation axis 312, which runs substantially parallel to the support column 301 and is likewise situated in the plane of the drawing in the embodiment example of FIG. 3. The second carrier arm 307 is mounted on the lift arm carrier 305 with the joint 308 on a pivot axis 313, which is oriented orthogonally of the rotation axis 312 of the lift arm carrier 305, and runs perpendicularly to the plane of the drawing in the embodiment example shown. This arrangement of the pivot axis 313 makes it possible, for example, to move the carrier arm 307 in the support 300 out of a pivoting position A into a pivoting position B indicated by dashed lines.

In order to compensate the weight acting on the operation microscope 309 and bringing about a corresponding load moment on the pivot axis 313, a counterweight 314 is provided in the support 300, and serves as the means to produce a restoring force. This counterweight 314 is arranged in the region of the support column 301. Thus the mass center of gravity of the whole system is also situated in the neighborhood of the rotation axis 311 of the rotary joint 302 of the support column 301, and the inertial effect of the counterweight 314 is minimized.

The counterweight 314 is connected to the second carrier arm 307 via a rod arrangement as coupling means. This rod arrangement includes a lever arm 315 carrying the counterweight 314 and mounted on a rotation axis 316 oriented perpendicular to the support column 301 and to the first carrier arm 304. This lever arm 315 includes a ball joint 317, which is situated on the side opposite the counterweight 314 with respect to the rotation axis 316. A transmission rod 318 is connected to this ball joint 317, and is guided along the rotation axis 312 of the rotary joint 306 in the lift arm carrier 305. This transmission rod 318 is fastened with a ball joint 319 to the second carrier arm 307. Thus a movement of the operation microscope 309 out of a pivoting position A into a pivoting position A' is coupled to a corresponding movement of the counterweight 314 out of a position B into a position B' indicated by dashed lines. A moment on the rotation axis 313 of the second carrier arm 307, which is brought about by a weight acting on the operation microscope 309, is thus opposed by a moment produced by means of the counterweight 314.

The ball joint 317 comprises a joint ball with a sleeve that receives the lever arm 315 for free displacement. The ball joint 319 on the second carrier arm 307 is constituted in a corresponding manner. The transmission rod 318 is displaceably guided between the rollers 320 and 321 along the rotation axis 312, and includes a freewheel rotary joint 322. The freewheel rotary joint 322 can be constituted in a corresponding manner to the freewheel rotary joint 121 of FIG. 1. It divides the transmission rod 318 into a section 324 which is allocated to the second carrier arm 307 and a section 323 which faces toward the counterweight 314.

The freewheel rotary joint 322 has the effect that the respective sections 323 and 324 of the transmission rod 318 are freely rotatable with respect to one another. Thus a rotational movement of the second carrier arm 307 around the rotation axis 312 of the lift arm carrier 3 05 with the rotary joint 306 is decoupled from a movement of the counterweight 314. In particular, a feedback of this rotary motion in the rod arrangement to the counterweight 314 is suppressed.

We claim:

1. A support comprising:
a support column,
a first carrier arm,
a second carrier arm mounted pivotably with respect to said first carrier arm, on a first axis and a second axis,
a restoring device for producing a restoring force around said first axis,
a coupling device that couples said second carrier arm with said restoring device, and
a suppressing device that suppresses feedback of movement of said second carrier arm around said first axis to said restoring device,
wherein said restoring device comprises a weight, and
wherein said coupling device comprises a cable connection.

2. A support comprising:
a support column,
a first carrier arm,
a second carrier arm mounted pivotably with respect to said first carrier arm, on a first axis and a second axis,
a restoring device for producing a restoring force around said first axis,
a coupling device that couples said second carrier arm with said restoring device, and
a suppressing device that suppresses feedback of movement of said second carrier arm around said first axis to said restoring device,
wherein said restoring device comprises a weight,
wherein said coupling device comprises a cable connection, and
further comprising rollers that guide said cable connection sectionally along one of said first axis or said second axis.

3. A support comprising:
a support column,
a first carrier arm,
a second cater arm mounted pivotably with respect to said first carrier arm, on a first axis and a second axis,
a restoring device for producing a restoring force around said first axis,
a coupling device that couples said second carrier arm with said restoring device, and
a suppressing device that suppresses feedback of movement of said second carrier arm around said fast axis to said restoring device,
wherein said restoring device comprises a weight,
wherein said coupling device comprises a cable connection,
further comprising rollers that guide said cable connection sectionally along said first axis, and
wherein said support supports a medical operation microscope.

4. A support comprising:
a support column,
a first carrier arm which is mounted on the support column and can be rotated about a vertical rotation axis,
a second carrier arm mounted pivotably with respect to said first carrier arm on a first axis and a second axis,
a restoring device for producing a restoring force around said first axis, and
a coupling device that couples said second cater arm to said restoring device,
said restoring device comprising a weight that moves in a region of said column axis of said support column, and
wherein said coupling device comprises a cable connection.

5. A support comprising:
a support column,
a first carrier arm which is mounted on the support column and can be rotated about a vertical rotation axis,
a second carrier arm mounted pivotably with respect to said first carrier arm on a first axis and a second axis,
a restoring device for producing a restoring force around said first axis, and
a coupling device that couples said second carrier arm to said restoring device,
said restoring device comprising a weight that moves in a region of said column axis of said support column,
wherein the weight acts on said second carrier arm due to a load arranged on said second carrier arm, and said restoring device compensates said weight, and
wherein said restoring force is transmitted by a cable connection, and acts on said second carrier arm at a distance from said support column, and
wherein said cable connection is deflected into a direction parallel to said support column.

6. A support comprising:
a support column,
a first carrier arm which is mounted on the support column and can be rotated about a vertical rotation axis,
a second carrier arm mounted pivotably with respect to said first carrier arm on a first axis and a second axis,
a restoring device for producing a restoring force around said first axis, and
a coupling device that couples said second carrier arm to said restoring device,
said restoring device comprising a weight that moves in a region of said column axis of said support column,
wherein said coupling device comprises a cable connection, and
further comprising a deflector in the neighborhood of said support column for guiding said cable connection.

7. A support comprising:
a support column,
a first carrier arm which is mounted on the support column and can be rotated about a vertical rotation axis,
a second carrier arm mounted pivotably with respect to said first carrier arm on a first axis and a second axis,
a restoring device for producing a restoring force around said first axis, and
a coupling device that couples said second carrier arm to said restoring device,
said restoring device comprising a weight that moves in a region of said column axis of said support column,
wherein said coupling device comprises a cable connection, and
further comprising rollers that guide said cable connection sectionally along said first axis.

* * * * *